United States Patent
Isono

(10) Patent No.: US 11,491,097 B2
(45) Date of Patent: Nov. 8, 2022

(54) PRODUCTION METHOD FOR MEDICAL AND COSMETIC MATERIAL, AND MEDICAL AND COSMETIC MATERIAL

(71) Applicant: DAINICHISEIKA COLOR & CHEMICALS MFG. CO., LTD., Tokyo (JP)

(72) Inventor: Yasuyuki Isono, Tokyo (JP)

(73) Assignee: DAINICHISEIKA COLOR & CHEMICALS MFG. CO., LTD., Tokyo (JP)

(*) Notice: Subject to any disclaimer, the term of this patent is extended or adjusted under 35 U.S.C. 154(b) by 0 days.

(21) Appl. No.: 16/636,547

(22) PCT Filed: Aug. 16, 2018

(86) PCT No.: PCT/JP2018/030400
§ 371 (c)(1),
(2) Date: Feb. 4, 2020

(87) PCT Pub. No.: WO2019/044519
PCT Pub. Date: Mar. 7, 2019

(65) Prior Publication Data
US 2021/0154126 A1    May 27, 2021

(30) Foreign Application Priority Data
Sep. 4, 2017 (JP) .............................. JP2017-169099

(51) Int. Cl.
*A61K 8/73* (2006.01)
*A61K 8/02* (2006.01)
*A61Q 19/08* (2006.01)

(52) U.S. Cl.
CPC ............ *A61K 8/735* (2013.01); *A61K 8/0204* (2013.01); *A61K 8/731* (2013.01); *A61K 8/733* (2013.01); *A61Q 19/08* (2013.01); *A61K 2800/87* (2013.01)

(58) Field of Classification Search
CPC .................................................... A61K 8/735
See application file for complete search history.

(56) References Cited

U.S. PATENT DOCUMENTS

| | | | |
|---|---|---|---|
| 2006/0194758 A1 | 8/2006 | Lebreton | |
| 2011/0003769 A1 | 1/2011 | Kim et al. | |
| 2015/0272850 A1 | 10/2015 | Yoneto et al. | |
| 2016/0081906 A1* | 5/2016 | Yoneto | ............... A61K 8/73 |
| 2016/0208064 A1* | 7/2016 | Isono | ............... C08J 7/14 |
| 2018/0000994 A1 | 1/2018 | Isono et al. | |
| 2018/0021482 A1 | 1/2018 | Isono et al. | |

FOREIGN PATENT DOCUMENTS

| | | | |
|---|---|---|---|
| JP | 10-298054 | 11/1998 | |
| JP | 3215852 | 10/2001 | |
| JP | 2007-297460 | 11/2007 | |
| JP | 2007297460 A * | 11/2007 | ............... A61K 8/73 |
| JP | 2008-179629 | 8/2008 | |
| JP | 2010-082401 | 4/2010 | |
| JP | 2011-513481 | 4/2011 | |
| JP | 2014-024828 | 2/2014 | |
| JP | 2016-166133 | 9/2016 | |
| JP | 2016166133 A * | 9/2016 | ............... A61K 8/02 |
| JP | 2016-175853 | 10/2016 | |
| KR | 10-2016-0048876 | 5/2016 | |
| WO | 2009/036120 | 3/2009 | |
| WO | 2009/113820 | 9/2009 | |
| WO | 2015/002091 | 1/2015 | |
| WO | 2016/136885 | 9/2016 | |
| WO | 2016/136886 | 9/2016 | |

OTHER PUBLICATIONS

JP2007297460A, Google English Translation, downloaded in Apr. 2021 (Year: 2021).*
JP2016166133A, Google English Translation, downloaded in Apr. 2021 (Year: 2021).*
Australian Examination Report, issued in the corresponding Auslialian patent application No. 2018326846, dated Jul. 30, 2020, 5 pages.
International Preliminary Report on Patentability, issued in the corresponding PCT application No. PCT/JP2018/030400, dated Mar. 10, 2020, 18 pages.
International Search Report, issued in the corresponding PCT application No. PCT/JP2018/030400, dated Nov. 6, 2018, 5 pages.
Indian Office Action, issued in the corresponding Indian patent application No. 202017012921, dated Jan. 4, 2021, 5 pages.
European Office Action, issued in the corresponding European patent application No. 18851040.8, dated Aug. 16, 2022, 4 pages.

* cited by examiner

*Primary Examiner* — Mark V Stevens
*Assistant Examiner* — Alparslan Asan
(74) *Attorney, Agent, or Firm* — Hamre, Schumann, Mueller & Larson, P.C.

(57) ABSTRACT

The present invention provides a simple method for producing a medical/cosmetic sheet that is excellent in adhesion to skin or the like and sense of wearing, and is capable of releasing a functional component gradually and supplying it continuously to a treatment area or the like, and a medical/cosmetic sheet produced by this production method. Provided is a method for producing a medical/cosmetic material including a step of shaping a raw material containing a water-soluble salt of a first polyanionic polysaccharide having a viscosity-average molecular weight of 10,000 or lower, and a water-soluble salt of a second polyanionic polysaccharide having a viscosity-average molecular weight of 50,000 or higher, and thereby obtaining a water-soluble shaped body. A medical/cosmetic material produced by this production method is also provided.

5 Claims, 6 Drawing Sheets

[Figure 1]
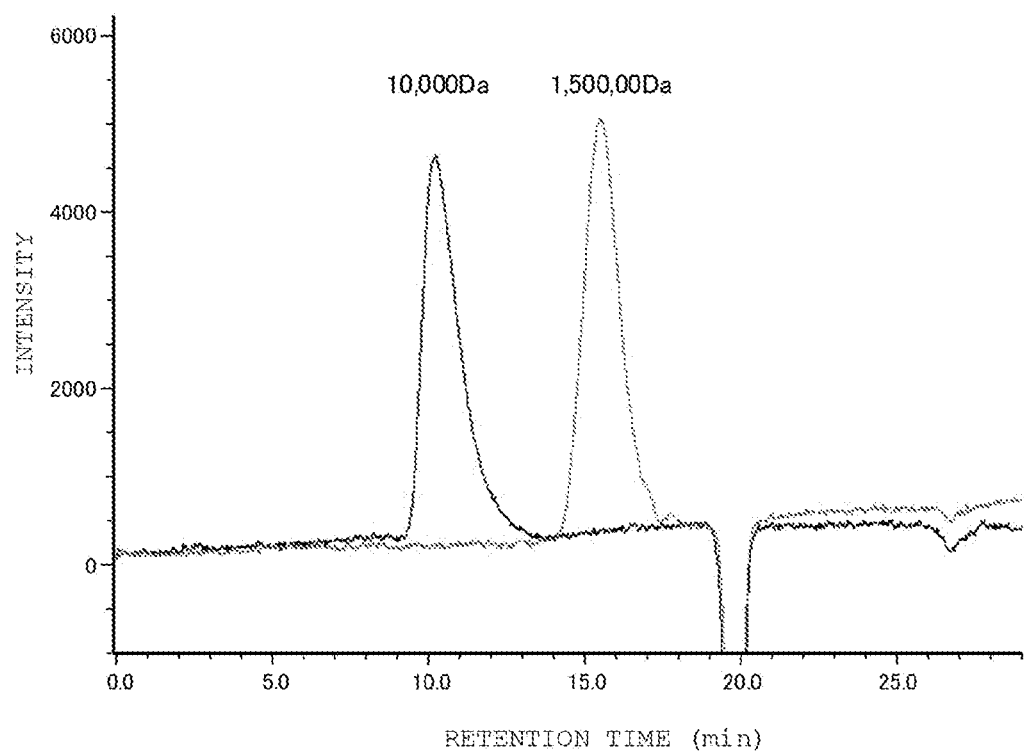

[Figure 2]
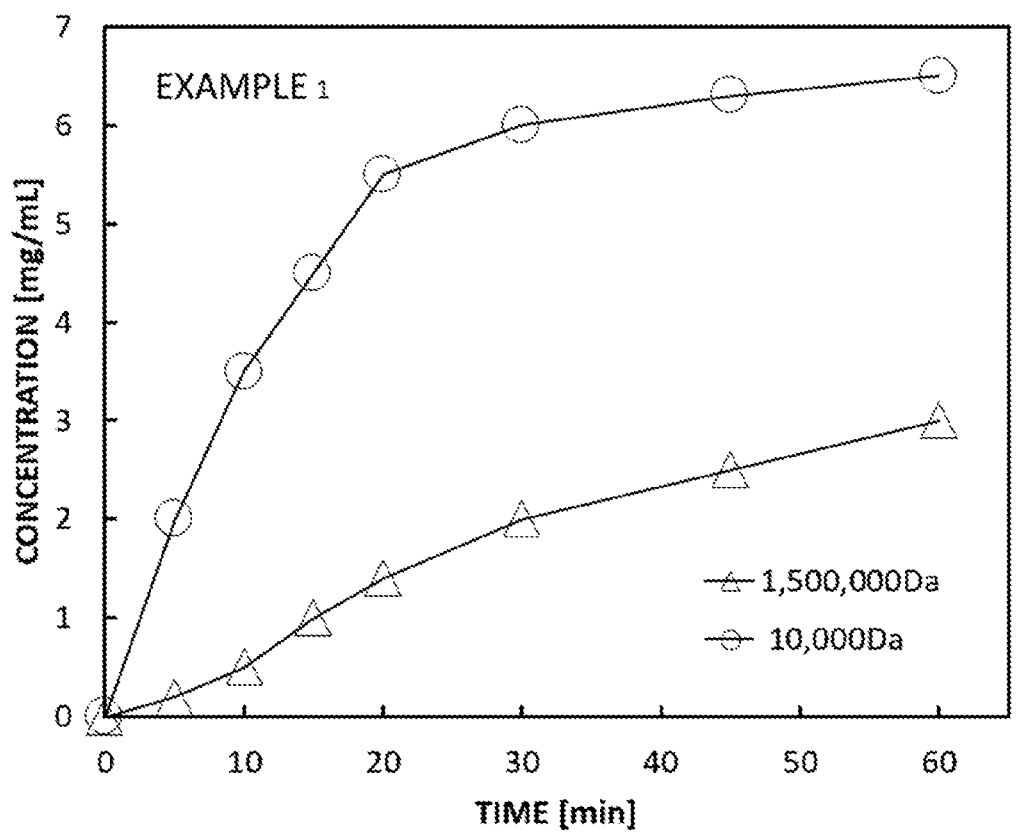

[Figure 3]
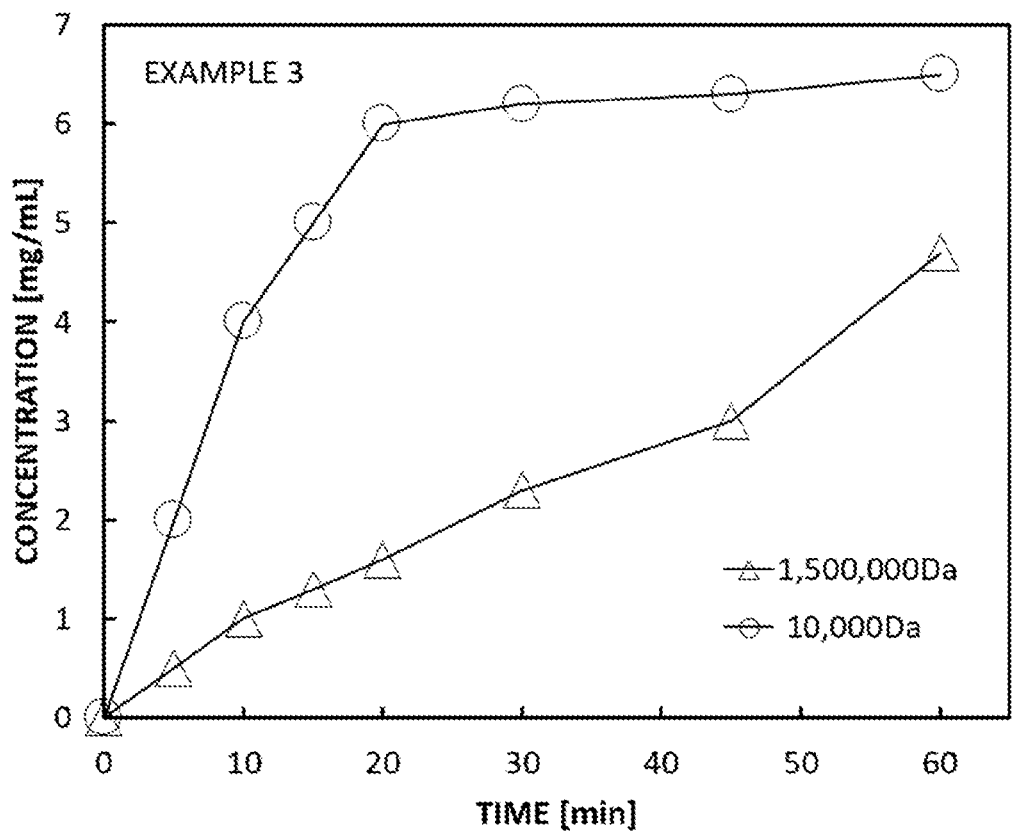

[Figure 4]
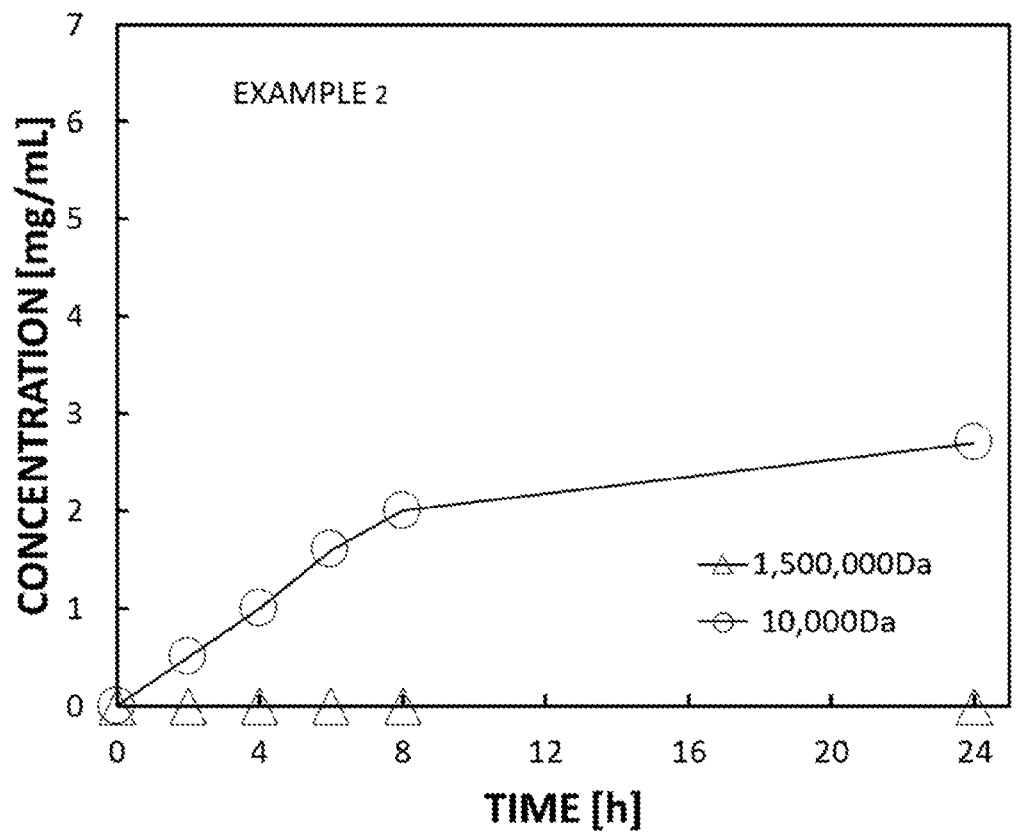

[Figure 5]
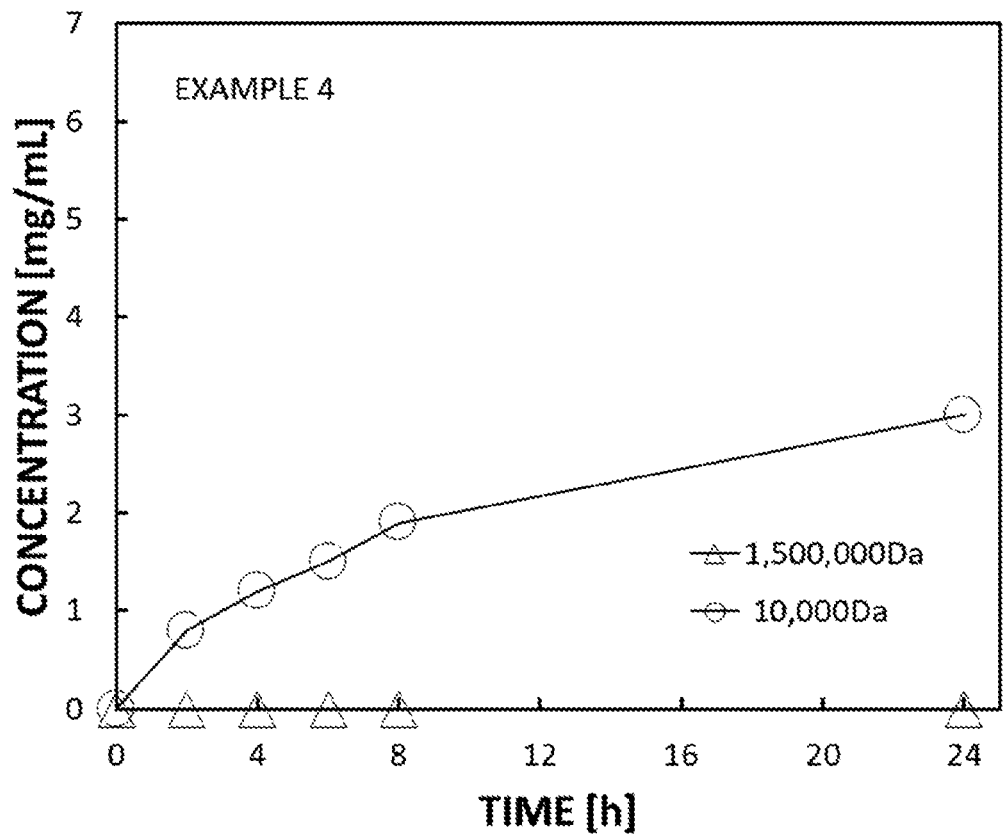

[Figure 6]
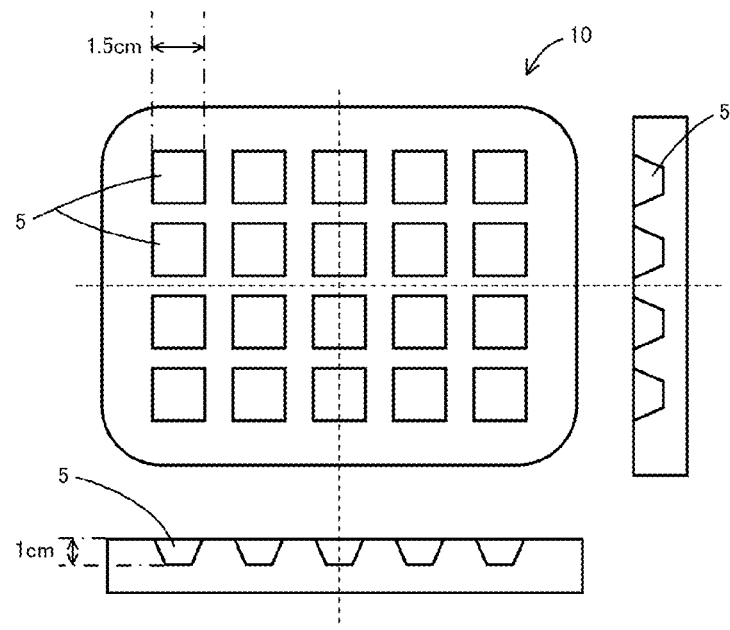

PRODUCTION METHOD FOR MEDICAL AND COSMETIC MATERIAL, AND MEDICAL AND COSMETIC MATERIAL

TECHNICAL FIELD

The present invention relates to a method for producing a medical/cosmetic material, and a medical/cosmetic material.

BACKGROUND ART

It is known that polyanionic polysaccharides, such as hyaluronic acid and alginic acid, exhibit moderate viscosity, adhesiveness, moisture retention, and biocompatibility. Therefore, these polyanionic polysaccharides and salts thereof are widely used as a raw material for medical materials, food materials, cosmetic materials, and the like. Among others, hyaluronic acid is excellent in characteristic physical properties, such as water retention; exhibits a high level of safety and biocompatibility; and therefore is utilized in various applications, such as food, cosmetics, and pharmaceutical products.

In addition, a cosmetic sheet (decorative sheet) intended to give moisture to skin and prevent wrinkles is attracting attention. For example, a wrinkle-improving sheet obtained by sticking a moisture-retaining agent or the like on wood fiber-derived paper is proposed (Patent Literature 1). Moreover, a decorative sheet obtained by allowing a net-like structure formed with a nanofiber made of hyaluronic acid to retain a moisture-retaining agent is proposed (Patent Literature 2). Further, an electrospun sheet obtained by allowing a base material composed of a water-soluble polysaccharide, such as hyaluronic acid, to contain a moisture-retaining component is proposed (Patent Literature 3).

CITATION LIST

Patent Literature

Patent Literature 1: Japanese Patent No. 3215852
Patent Literature 2: Japanese Patent Laid-Open No. 2008-179629
Patent Literature 3: International Publication No. WO2009036120

SUMMARY OF INVENTION

Technical Problem

However, the wrinkle-improving sheet proposed in Patent Literature 1 is easily broken because the base material is paper, and has been deficient in adhesion to skin and sense of wearing. In addition, the sheets proposed in Patent Literatures 2 and 3 need to be produced by an electrospinning method, and therefore production processes thereof have been complicated. Further, the sheets proposed in Patent Literatures 2 and 3 as well as the wrinkle-improving sheet proposed in Patent Literature 1 have been deficient in adhesion to skin and sense of wearing.

It is to be noted that desirably, a functional component, such as a polyanionic polysaccharide such as hyaluronic acid, and a salt thereof, is released gradually to be supplied continuously to a treatment area or an affected area. However, with respect to the sheets proposed in Patent Literatures 1 to 3, the sustained release of the functional component has not been studied at all.

The present invention has been completed in view of the problems of such conventional techniques, and an object of the present invention is to provide a simple method for producing a medical/cosmetic sheet that is excellent in adhesion to skin or the like and sense of wearing, and is capable of releasing a functional component gradually and supplying it continuously to a treatment area or the like. Another object of the present invention is to provide a medical/cosmetic sheet that is excellent in adhesion to skin or the like and sense of wearing, and is capable of releasing a functional component gradually and supplying it continuously to a treatment area or the like.

Solution to Problem

That is, according to the present invention, there is provided a method for producing a medical/cosmetic material, the method including a step of shaping a raw material containing: a water-soluble salt of a first polyanionic polysaccharide having a viscosity-average molecular weight of 10,000 or lower; and a water-soluble salt of a second polyanionic polysaccharide having a viscosity-average molecular weight of 50,000 or higher, thereby obtaining a water-soluble shaped body (hereinafter, also written as "the first production method").

In addition, according to the present invention, there is provided a method for producing a medical/cosmetic material including: a step of shaping a raw material containing: a water-soluble salt of a first polyanionic polysaccharide having a viscosity-average molecular weight of 10,000 or lower; and a water-soluble salt of a second polyanionic polysaccharide having a viscosity-average molecular weight of 50,000 or higher, thereby obtaining a water-soluble shaped body; and a step of subjecting the obtained water-soluble shaped body to a water-insolubilization treatment (also written as "the second production method").

Further, according to the present invention, there is provided a medical/cosmetic material produced by the first production method (hereinafter, also written as "the first medical/cosmetic material").

Moreover, according to the present invention, there is provided a medical/cosmetic material produced by the second production method (hereinafter, also written as "the second medical/cosmetic material").

Advantageous Effects of Invention

According to the present invention, a simple method for producing a medical/cosmetic sheet that is excellent in adhesion to skin or the like and sense of wearing, and is capable of releasing a functional component gradually and suppling it continuously to a treatment area or the like can be provided. In addition, according to the present invention, a medical/cosmetic sheet that is excellent in adhesion to skin or the like and sense of wearing, and is capable of releasing a functional component gradually and supplying it continuously to a treatment area or the like can be provided.

BRIEF DESCRIPTION OF DRAWINGS

FIG. 1 shows chromatograms obtained by analyzing sodium hyaluronate having a viscosity-average molecular weight of 1,500,000 (1,500,000 Da) and of 10,000 (10,000 Da).

FIG. 2 is a graph showing changes with time in concentrations of sodium hyaluronate dissolving out of a film produced in Example 1.

FIG. 3 is a graph showing changes with time in concentrations of sodium hyaluronate dissolving out of a film produced in Example 3.

FIG. 4 is a graph showing changes with time in concentrations of sodium hyaluronate dissolving out of a film produced in Example 2.

FIG. 5 is a graph showing changes with time in concentrations of sodium hyaluronate dissolving out of a film produced in Example 4.

FIG. 6 is a schematic diagram describing a shape of a tray used in Example 5.

DESCRIPTION OF EMBODIMENTS

Hereinafter, embodiments of the present invention will be described, but the present invention is not limited to the following embodiments.

<Medical/Cosmetic Material and Method for Producing Same>

A method for producing a medical/cosmetic material (the first production method) of the present invention includes a step of shaping a raw material containing: a water-soluble salt of a first polyanionic polysaccharide having a viscosity-average molecular weight of 10,000 or lower; and a water-soluble salt of a second polyanionic polysaccharide having a viscosity-average molecular weight of 50,000 or higher, thereby obtaining a water-soluble shaped body. In addition, the first medical/cosmetic material of the present invention is the one produced by the first production method. Further, a method for producing a medical/cosmetic material (the second production method) of the present invention includes: a step of shaping a raw material containing: a water-soluble salt of a first polyanionic polysaccharide having a viscosity-average molecular weight of 10,000 or lower; and a water-soluble salt of a second polyanionic polysaccharide having a viscosity-average molecular weight of 50,000 or higher, thereby obtaining a water-soluble shaped body; and a step of subjecting the obtained water-soluble shaped body to a water-insolubilization treatment. The second medical/cosmetic material of the present invention is the one produced by the second production method. Hereinafter, details on the medical/cosmetic material of the present invention and the method for producing the medical/cosmetic material of the present invention will be described.

The water-soluble shaped body is formed using a raw material containing a water-soluble salt of a polyanionic polysaccharide. The polyanionic polysaccharide is a polysaccharide having at least one negatively charged anionic group, such as a carboxy group or a sulfonate group, in a molecular structure thereof. In addition, the water-soluble salt of a polyanionic polysaccharide is obtained in such a way that at least part of the anionic groups in the polyanionic polysaccharide forms a salt. It is to be noted that the anionic group in the polyanionic polysaccharide may be the one introduced in the molecule of the polysaccharide.

Specific examples of the polyanionic polysaccharide include carboxyalkyl cellulose such as carboxymethyl cellulose and carboxyethyl cellulose, carboxymethyl starch, carboxymethylamylose, chondroitin sulfate (including chondroitin-4-sulfate and chondroitin-6-sulfate), hyaluronic acid, heparin, heparin sulfate, heparan sulfate, alginic acid, pectin, carrageenan, dermatan sulfate, and dermatan-6-sulfate. These polyanionic polysaccharides can be used singly, or two or more thereof can be used in combination.

Examples of the water-soluble salt of the polyanionic polysaccharide include inorganic salts, ammonium salts, and organic amine salts. Specific examples of the inorganic salts include: salts of an alkali metal such as sodium or potassium; alkali earth metal salts such as calcium salts; and salts of a metal such as zinc or iron.

The viscosity-average molecular weight of the water-soluble salt of the first polyanionic polysaccharide is 10,000 or lower, preferably 1,000 to 5,000. In addition, the viscosity-average molecular weight of the water-soluble salt of the second polyanionic polysaccharide is 50,000 or higher, preferably 100,000 to 2,000,000. By using two types of water-soluble salts of polyanionic polysaccharides each having a different viscosity-average molecular weight in combination, the medical/cosmetic sheet of the present invention that is excellent in adhesion to skin or the like and sense of wearing, and is capable of releasing a functional component gradually and supplying it continuously to a treatment area or the like can be obtained.

The viscosity-average molecular weight can be determined by a known measurement method. Specifically, a polyanionic polysaccharide or a salt thereof (dried product) is dissolved in a 0.2 M sodium chloride aqueous solution to determine the intrinsic viscosity ($\eta$) at 30±0° C. with a Ubellohde viscometer, and the viscosity-average molecular weight is calculated based on the Laurent equation ($\eta$ (intrinsic viscosity)=$3.6 \times 10^{-4} \cdot M^{0.78}$ (M: viscosity-average molecular weight). The intrinsic viscosity ($\eta$) is measured by Method I: Viscosity measurement by capillary tube viscometer of Viscosity Measurement, GENERAL TESTS in The Japanese Pharmacopoeia, Sixteenth Edition.

In the case of the first production method, a base material that is excellent in adhesion to skin or the like and sense of wearing is more specifically formed with the water-soluble salt of the high-molecular-weight second polyanionic polysaccharide, the water-soluble salt having a relatively large viscosity-average molecular weight. In the formed base material, the water-soluble salt of the low-molecular-weight first polyanionic polysaccharide, the water-soluble salt having a relatively small viscosity-average molecular weight, is retained. Therefore, it is considered that the water-soluble salt of the first polyanionic polysaccharide is released gradually from the base material to be supplied continuously to a treatment area or the like.

In addition, in the case of the second production method, a water-insoluble base material that is excellent in adhesion to skin or the like and sense of wearing is more specifically formed in such a way that a base material formed with the water-soluble salt of the high-molecular-weight second polyanionic polysaccharide, the water-soluble salt having a relatively large viscosity-average molecular weight, is subjected to a water-insolubilization treatment. On the other hand, the water-soluble salt of the lower-molecular-weight first polyanionic polysaccharide has a relatively small viscosity-average molecular weight, therefore hardly constitutes the base material even if it is subjected to a water-insolubilization treatment, and gets into a state of being retained in the base material formed with the high-molecular-weight second polyanionic polysaccharide. Therefore, it is considered that the low-molecular-weight polyanionic polysaccharide is released gradually from the base material to be supplied continuously to a treatment are or the like.

The amount of the water-soluble salt of the first polyanionic polysaccharide contained in the raw material for obtaining the water-soluble shaped body (the first medical/cosmetic material) is preferably 1 to 150 parts by mass, more preferably 10 to 100 parts by mass based on 100 parts by mass of the water-soluble salt of the second polyanionic polysaccharide. When the amount of the water-soluble salt of the first polyanionic polysaccharide is less than 1 part by mass based on 100 parts by mass of the water-soluble salt of the second polyanionic polysaccharide, the amount of the functional component to be released is made small, and the effects as a medical/cosmetic sheet are somewhat deficient in some cases. On the other hand, when the amount of the water-soluble salt of the first polyanionic polysaccharide exceeds 150 parts by mass based on 100 parts by mass of the water-soluble salt of the second polyanionic polysaccharide, the amount of the base material to retain the functional component is made small, and therefore handling properties and strength are somewhat deteriorated in some cases.

The first medical/cosmetic material being a water-soluble shaped body can be obtained by, for example, shaping a raw material (aqueous solution) obtained by dissolving a water-soluble salt of a polyanionic polysaccharide in water into a desired shape and then drying a resultant shaped body. Examples of the shape of the water-soluble shaped body include a sheet-like shape, a film-like shape, a sponge-like shape, a powdery shape, and a string-like shape. The second medical/cosmetic material having a shape, such as a sheet-like shape, a film-like shape, a sponge-like shape, a powdery shape, or a string-like shape, according to the application can be obtained by subjecting the water-soluble shaped body having any one of these shapes to a water-insolubilization treatment. It is to be noted that if necessary, the obtained medical/cosmetic material may further be shaped to be processed into a desired shape.

For example, a sheet-like, film-like, or sponge-like water-soluble shaped body can be obtained by pouring a raw material (aqueous solution) into a suitable container and then drying or freeze-drying the raw material (aqueous solution). A fiber-like water-soluble shaped body can be obtained by extruding a raw material (aqueous solution) into a poor solvent from a nozzle. A string-like raw material-shaped body can be obtained by filling a suitable tube with a raw material (aqueous solution) and then drying or freeze-drying the raw material (aqueous solution). In this way, according to the production method of the present invention, a medical/cosmetic material having a shape according to the application can be obtained.

In the second production method, the method of subjecting the water-soluble shaped body to a water-insolubilization treatment is not particularly limited, and a conventionally known method can be adopted. Specific examples of the method of subjecting the water-soluble shaped body to a water-insolubilization treatment include: a method of water-insolubilizing the water-soluble shaped body by chemically crosslinking the water-soluble shaped body using a crosslinking agent; a method of water-insolubilizing the water-soluble shaped body by irradiating the water-soluble shaped body with an electron beam to crosslink the water-soluble shaped body; a method of water-insolubilizing the water-soluble shaped body by crosslinking the water-soluble shaped body through ionic bonds using a polyvalent metal ion; and a method of water-insolubilizing the water-soluble shaped body by bringing the water-soluble shaped body into contact with a treatment liquid containing an acid anhydride. Among others, the method of bringing a raw material-shaped body into contact with a treatment liquid containing an acid anhydride is preferable because the method is simple and can subject the water-soluble shaped body to a water-insolubilization treatment sufficiently and quickly. It is to be noted that the reaction mechanism or the like supposed in the case where the water-soluble shaped body formed using a water-soluble salt of a polyanionic polysaccharide is treated with a treatment liquid containing an acid anhydride, such as acetic anhydride, is disclosed in, for example, International Publication No. WO 2015029892, Japanese Patent Laid-Open No. 2016-163695, and the like.

Specific examples of the acid anhydride for use in the treatment liquid include acetic anhydride, propionic anhydride, succinic anhydride, butyric anhydride, phthalic anhydride, and maleic anhydride. Among others, acetic anhydride and propionic anhydride are preferable. These acid anhydrides can be used singly, or two or more thereof can be used in combination.

The treatment liquid preferably further contains at least any one of media of water and water-soluble organic solvents, and the acid anhydride is preferably dissolved or dispersed in this medium. By using the treatment liquid in which the acid anhydride is dissolved or dispersed in such a medium, the water-soluble shaped body can be water-insolubilized sufficiently and quickly.

Specific examples of the water-soluble organic solvents include methanol, ethanol, propanol, dimethyl sulfoxide (DMSO), acetonitrile, and tetrahydrofuran. Among them, methanol, ethanol, and dimethyl sulfoxide are preferable. These water-soluble organic solvents can be used singly, or two or more thereof can be used in combination.

The concentration of the acid anhydride in the treatment liquid is usually 0.1 to 50% by mass and is preferably 5 to 30% by mass. When the concentration of the acid anhydride is less than 0.1% by mass, the extent of water-insolubilization of a resultant second medical/cosmetic material is made insufficient, or there is a tendency that the water-insolubilization requires a long time. On the other hand, when the concentration of the acid anhydride exceeds 50% by mass, there is a tendency that the effects hit the ceiling.

It is to be noted that the polyanionic polysaccharide has a high hydrophilicity, and therefore the treatment liquid preferably contains water as a medium from the viewpoint of water-insolubilizing the water-soluble shaped body more sufficiently and quickly. The content of water in the treatment liquid is preferably set to such an extent that the water-soluble shaped body does not dissolve or swell. Specifically, the content of water in the treatment liquid is preferably 0.01 to 50% by mass, more preferably 5 to 20% by mass. When the content of water in the treatment liquid is less than 0.01% by mass, the water-insolubilization is made insufficient in the solvents other than methanol in some cases. In addition, when the content of water in the treatment liquid exceeds 50% by mass, keeping the shape of a resultant medical/cosmetic material is made difficult in some cases.

In the water-insolubilization step, it is preferable to water-insolubilize the water-soluble shaped body by bringing the water-soluble shaped body into contact with the treatment liquid containing an acid anhydride. By bringing the water-soluble shaped body into contact with the treatment liquid, the water-soluble shaped body can be water-insolubilized while keeping the shape thereof, and a medical/cosmetic material having a corresponding shape can be obtained. The method of bringing the water-soluble shaped body into contact with the treatment liquid is not particularly limited, but it is preferable to perform the treatment in such a way that the treatment liquid comes into contact with the whole water-soluble shaped body and the treatment liquid penetrates the inside of the water-soluble shaped body. Specific treatment methods include methods such as immersing the water-soluble shaped body in the treatment liquid and applying or spraying (nebulizing) the treatment liquid to the water-soluble shaped body.

The temperature during the water-insolubilization treatment is not particularly limited as long as the temperature does not exceed the boiling point of the treatment liquid. It is preferable to set the temperature during the treatment to 0 to 80° C., more preferably 0 to 70° C., and particularly preferably room temperature (25° C.) to 60° C. from the viewpoint of suppressing the decomposition and denaturation of the polyanionic polysaccharide and from the viewpoint of suppressing the volatilization of the medium, byproducts, and the like. However, when the treatment is conducted under the condition in which the treatment liquid does not volatilize during the treatment, for example, the treatment is conducted with a heat press, a heat roller, or the like, the treatment can be conducted in a shorter time without causing the decomposition and denaturation, and the like. For example, in the case where the treatment is conducted with a heat press, a heat roller, or the like, it is preferable to set the temperature during the treatment to 50 to 90° C. and to set the treatment time to 30 minutes or shorter. In the second production method, after the water-insolubilization treatment is completed, the second medical/cosmetic material can be obtained, if necessary, through washing or the like with water or a water-soluble organic solvent.

When the water-soluble shaped body is brought into contact with the treatment liquid containing an acid anhydride to be subjected to a water-insolubilization treatment, that is, when the water-soluble shaped body is subjected to a water-insolubilization treatment without using a crosslinking agent, a structure of a functional group or the like derived from the crosslinking agent is not incorporated into the molecule that constitutes a resultant medical/cosmetic material. Therefore, the second medical/cosmetic material obtained by bringing the water-soluble shaped body into contact with the treatment liquid containing an acid anhydride, thereby subjecting the water-soluble shaped body to a water-insolubilization treatment is more suitable as a medical/cosmetic material because the characteristics inherent in the polyanionic polysaccharide which is a raw material is retained therein and the safety thereof is higher. It is to be noted that the thickness of the medical/cosmetic material is not particularly limited, but is preferably 20 to 200 μm, more preferably 60 to 120 μm.

The "water-insolubility" in the present specification means a characteristic of not easily dissolving in water. More specifically, with respect to the second medical/cosmetic material of the present invention, the mass of a dried body obtained by repeating twice the operation in which the second medical/cosmetic material is made into a swollen state with water and is then dried is 80% or more of the dry mass before this operation.

The swelling ratio of the second medical/cosmetic material of the present invention is preferably 6,000% by mass or less, more preferably 900% by mass or less, particularly preferably 100 to 500% by mass, and most preferably 150 to 350% by mass. The "swelling ratio" in the present specification means a ratio (% by mass) of the "mass of the second medical/cosmetic material after retaining water (after swelling)" to the "mass of the second medical/cosmetic material before retaining water (before swelling)". It is to be noted that the second medical/cosmetic material having a relatively low swelling ratio (for example, of 6,000% by mass or less) can be produced by increasing the amount of water in the treatment liquid to be used in the water-insolubilization step within a range not exceeding, for example, 20% by mass. In addition, the second medical/cosmetic material having a relatively low swelling ratio (for example, of 6,000% by mass or less) can be produced by increasing the amount of the acid anhydride in the treatment liquid (for example, the upper limit is 20% by mass).

In the case where the water-soluble shaped body is water-insolubilized by bringing the water-soluble shaped body into contact with the treatment liquid containing an acid anhydride, molecules of the polyanionic polysaccharide that constitutes a resultant second medical/cosmetic material are not substantially crosslinked. Further, a new covalent bond is not substantially formed in the polyanionic polysaccharide. However, it is inferred that a physical bond, such as a hydrogen bond, a hydrophobic bond, and Van der Waals force, is formed between the molecules of the polyanionic polysaccharide. Whether such a physical bond is formed between the molecules of the polyanionic polysaccharide can be checked by measuring an infrared absorption spectrum.

The second medical/cosmetic material of the present invention is water-insoluble stably in a wide pH region from acidity to alkalinity. However, the second medical/cosmetic material of the present invention, when, for example, brought into contact with or immersed in an aqueous medium having a pH of 12 or higher, can easily dissolves because the physical bond between molecules dissociates. In addition, it is harder to water-insolubilize the water-soluble salt of the first polyanionic polysaccharide as compared to the water-soluble salt of the second polyanionic polysaccharide. Therefore, in the second medical/cosmetic material of the present invention, the water-soluble salt of the first polyanionic polysaccharide relatively easily dissolves out of the base material composed of the second polyanionic polysaccharide which has been water-insolubilized.

EXAMPLES

Hereinafter, the present invention will be described specifically based on Examples, but the present invention is not limited to these Examples. It is to be noted that "parts" and "%" in Examples and Comparative Examples are each on a mass basis unless otherwise noted.

<Medical/Cosmetic Material Production (1)>

Example 1

By mixing 1 g of a powder of sodium hyaluronate (viscosity-average molecular weight of 1,500,000 Da, manufactured by Kikkoman Biochemifa Company), 1 g of a powder of sodium hyaluronate (viscosity-average molecular weight of 10,000 Da, manufactured by Kikkoman Biochemifa Company), 0.5 g of glycerin (the Japan Pharmacopoeia), and 97.5 g of water, 100 g of an aqueous solution was prepared. In a stainless steel tray of 12 cm in length×10 cm in width, 100 g of the prepared aqueous solution was cast and dried in a thermostatic chamber of 20° C. to obtain a film (water-soluble film) containing glycerin and having a thickness of about 50 μm.

Example 2

The water-soluble film produced in Example 1 was immersed in a treatment liquid (acetic anhydride:ethanol=20:80) to be left standing at 50° C. for 1 hour and was thereby subjected to a water-insolubilization treatment to obtain a film having a thickness of about 55 μm.

Example 3

By mixing 1 g of a powder of sodium hyaluronate (viscosity-average molecular weight of 1,500,000 Da, manufactured by Kikkoman Biochemifa Company), 1 g of a powder of sodium hyaluronate (viscosity-average molecular weight of 10,000 Da, manufactured by Kikkoman Biochemifa Company), and 98 g of water, 100 g of an aqueous solution was obtained. In a stainless steel vat, the prepared aqueous solution was cast and frozen at −30° C., and was then freeze-dried at a shelf-heating temperature of 120° C. to obtain a sponge-like shaped body (water-soluble shaped body).

Example 4

The water-soluble shaped body produced in Example 3 was immersed in a treatment liquid (acetic anhydride:methanol=10:90) to be left standing at room temperature for 18 hours and was thereby subjected to a water-insolubilization treatment. Subsequently, a resultant product was washed with methanol, an 80% by volume methanol aqueous solution, and water in the mentioned order to obtain a sponge-like shaped body.

<Evaluation>

(Measurement of Concentration of Sodium Hyaluronate)

The concentration of sodium hyaluronate in a sample (10 µL) prepared by dissolving an object of measurement with a 0.3% NaOH aqueous solution was measured using an HPLC system having the following constitution. FIG. 1 shows chromatograms obtained by analyzing sodium hyaluronate having a viscosity-average molecular weight of 1,500,000 Da and sodium hyaluronate having a viscosity-average molecular weight of 10,000 Da.

[HPLC System]

Pump: trade name "PU-980" (manufactured by JASCO Corporation)

Autosampler: trade name "AS-950-10" (manufactured by JASCO Corporation)

Column oven: trade name "CO-965" (manufactured by JASCO Corporation)

UV detector: trade name "UV-970" (manufactured by JASCO Corporation)

GPC column: trade name "TSKgel PWXL (diameter of 4.6 mm×300 mm×2 columns, manufactured by Tosoh Corporation)

Mobile phase: 0.1N NaCl aqueous solution

Flow rate: 1.0 mL/min

Column temperature: 40° C.

(Dissolution Study (1))

The films produced in Examples 1 and 3 were each cut to prepare test pieces of 2 cm×2 cm. The prepared test pieces were each put into a container having a diameter of 3.5 cm and a depth of 1.5 cm, and 5 mL of a PBS buffer solution (pH of 6.8) was added thereto. Each of these containers was put into a thermostatic chamber adjusted to 37° C. to be left standing. The buffer solution was taken out over time to measure the concentration of sodium hyaluronate. FIGS. 2 and 3 show the results of measuring the concentration of sodium hyaluronate in the buffer solution. As shown in FIGS. 2 and 3, the low-molecular-weight sodium hyaluronate dissolved out quickly, and then the high-molecular-weight sodium hyaluronate dissolved out slowly in the films produced in Examples 1 and 3. Thereby, it is found that a medical/cosmetic sheet from which the low-molecular-weight sodium hyaluronate which has a high penetrability to skin is released quickly, and the high-molecular-weight sodium hyaluronate dissolves gradually to form a coating film, thereby capable of protecting the surface or the like of the skin, can be provided.

(Dissolution Study (2))

The films produced in Examples 2 and 4 were each cut to prepare test pieces of 2 cm×2 cm. The prepared test pieces were each put into a container having a diameter of 3.5 cm and a depth of 1.5 cm, and 5 mL of a PBS buffer solution (pH of 6.8) was added thereto. Each of these containers was put into a thermostatic chamber adjusted to 37° C., and was shaken using a shaker at 10 to 20 rpm for 24 hours. The buffer solution was taken out over time to measure the concentration of sodium hyaluronate. FIGS. 4 and 5 show the results of measuring the concentration of sodium hyaluronate in the buffer solution. As shown in FIGS. 4 and 5, dissolving-out of the low-molecular-weight sodium hyaluronate was detected, but dissolving-out of the high-molecular-weight sodium hyaluronate was not detected in the films produced in Examples 2 and 4. Thereby, it is found that a medical/cosmetic sheet from which the low-molecular-weight sodium hyaluronate is released quickly, thereby supplying the low-molecular-weight sodium hyaluronate continuously to a treatment area or the like, and which is capable of protecting the surface of skin or of an internal organ by the high-molecular-weight sodium hyaluronate can be provided.

<Medical/Cosmetic Material Production (2)>

Example 5

By mixing 1 g of a powder of sodium hyaluronate (viscosity-average molecular weight of 1,500,000 Da, manufactured by Kikkoman Biochemifa Company), 0.5 g of a powder of sodium hyaluronate (viscosity-average molecular weight of 5,000 Da, manufactured by Kikkoman Biochemifa Company), and 98.5 g of water, 100 g of an aqueous solution was prepared. A polyethylene terephthalate tray 10 provided with 20 holes 5 each having a side of 1.5 cm and a depth of 1 cm, as shown in FIG. 6, was prepared. The prepared aqueous solution was cast into the holes 5 of this tray 10 in an amount of 1 mL for each hole 5 and was then placed in a freezer of −80° C. to be frozen. Frozen products obtained were subjected to vacuum-freeze drying (degree of vacuum of −20 Pa, shelf temperature of 25° C.) to obtain 20 pieces of sponge-like solids. A piece of the obtained sponge-like solids was placed on the back of a hand and was spread with a lotion. Thereby, it was found that the low-molecular-weight sodium hyaluronate is supplied to skin, and skin-protecting and moisture-retaining effects by the high-molecular-weight sodium hyaluronate are obtained.

Example 6

A sponge-like solid composed of high-molecular-weight sodium alginate/low-molecular-weight sodium hyaluronate was obtained in the same manner as in previously described Example 5, except that sodium alginate (viscosity-average molecular weight of 400,000 Da, manufactured by FUJIFILM Wako Pure Chemical Corporation) was used in place of sodium hyaluronate (viscosity-average molecular weight of 1,500,000 Da).

Example 7

A sponge-like solid composed of high-molecular-weight sodium carboxymethyl cellulose/low-molecular-weight sodium hyaluronate was obtained in the same manner as in previously described Example 5, except that sodium carboxymethyl cellulose (viscosity-average molecular weight of 150,000 Da, manufactured by Tokyo Chemical Industry Co., Ltd.) was used in place of sodium hyaluronate (viscosity-average molecular weight of 1,500,000 Da).

INDUSTRIAL APPLICABILITY

The medical/cosmetic material of the present invention is useful as a medical/cosmetic material because it is easy for a low-molecular-weight polyanionic polysaccharide (or a salt thereof), which easily penetrates into skin, to dissolve out efficiently, and a high-molecular-weight polyanionic polysaccharide (or a salt thereof), which exhibits a high protection effect, is retained in a treatment area over long hours.

REFERENCE SIGNS LIST

5: Hole
10: Tray

The invention claimed is:

1. A method for producing a medical/cosmetic material, the method comprising:
shaping a raw material comprising:
a water-soluble salt of a first polyanionic polysaccharide having a viscosity-average molecular weight in a range from 1,000 Da to 10,000 Da; and
a water-soluble salt of a second polyanionic polysaccharide having a viscosity-average molecular weight in a range from 100,000 Da to 2,000,000 Da, thereby obtaining a water-soluble shaped body; and
subjecting the obtained water-soluble shaped body to a water-insolubilization treatment by bringing the water-soluble shaped body into contact with a treatment liquid comprising an acid anhydride in a range from 5 to 50% by mass relative to the treatment liquid so as to form a water-insolubilized shaped body as the medical/cosmetic material,
wherein both the first polyanionic polysaccharide and the second polyanionic polysaccharide are hyaluronic acid,
an amount of the water-soluble salt of the first polyanionic polysaccharide is in a range from 1 to 150 parts by mass relative to 100 parts by mass of the water-soluble salt of the second polyanionic polysaccharide,
in the water-insolubilized shaped body, a water-insolubilized material of the water-soluble salt of the second polyanionic polysaccharide obtained by the water-insolubilization treatment forms a base material that retains therein, a water-insolubilized material of the water-soluble salt of the first polyanionic polysaccharide obtained by the water-insolubilization treatment,
the water-insolubilization treatment reduces dissolving in water of the water-soluble salt of the first polyanionic polysaccharide and the water-soluble salt of the second polyanionic polysaccharide, released from the water-insolubilized shaped body, compared with dissolving in water thereof released from the water-soluble shaped body before the water-insolubilization treatment, and
in a PBS buffer having pH 6.8 at 37° C., an amount of the water-soluble salt of the first polyanionic polysaccharide released from the water-insolubilized shaped body within 24 hours is more than an amount thereof released from the water-soluble shaped body within 5 minutes and less than an amount thereof released from the water-soluble shaped body within 20 minutes, and a dissolution of the water-soluble salt of the first polyanionic polysaccharide from the water-insolubilized shaped body is faster than a dissolution of the water-soluble salt of the second polyanionic polysaccharide from the water-insolubilized shaped body.

2. The method for producing a medical/cosmetic material according to claim 1,
wherein the acid anhydride is at least one material selected from the group consisting of acetic anhydride and propionic anhydride.

3. The method for producing a medical/cosmetic material according to claim 1,
wherein the water-soluble shaped body is in a sheet form, in a film form, in a sponge form, in a powder form, or in a string form.

4. The method for producing a medical/cosmetic material according to claim 1, wherein the amount of the water-soluble salt of the first polyanionic polysaccharide released from the water-insolubilized shaped body within 24 hours is more than the amount thereof released from the water-soluble shaped body within 5 minutes and less than an amount thereof released from the water-soluble shaped body within 15 minutes.

5. A medical/cosmetic material produced by the production method according to claim 1.

* * * * *